(12) United States Patent
Bhaskaran et al.

(10) Patent No.: US 9,775,825 B2
(45) Date of Patent: Oct. 3, 2017

(54) METHOD OF MANAGING CHEMOTHERAPY INDUCED ALOPECIA OR CACHEXIA OR BOTH

(75) Inventors: Sunil Bhaskaran, Pune (IN); Mohan Vishwaraman, Pune (IN)

(73) Assignee: Indus Biotech Private Limited, Pune, Maharashtra (IN)

( * ) Notice: Subject to any disclaimer, the term of this patent is extended or adjusted under 35 U.S.C. 154(b) by 141 days.

(21) Appl. No.: 14/233,510

(22) PCT Filed: Jul. 17, 2012

(86) PCT No.: PCT/IB2012/053646
§ 371 (c)(1),
(2), (4) Date: Jan. 17, 2014

(87) PCT Pub. No.: WO2013/011458
PCT Pub. Date: Jan. 24, 2013

(65) Prior Publication Data
US 2014/0187624 A1   Jul. 3, 2014

(30) Foreign Application Priority Data

Jul. 19, 2011 (IN) .................... 2058/MUM/2011

(51) Int. Cl.
*A61K 31/352* (2006.01)
(52) U.S. Cl.
CPC ............................. *A61K 31/352* (2013.01)
(58) Field of Classification Search
None
See application file for complete search history.

(56) References Cited

U.S. PATENT DOCUMENTS

| 4,698,360 A | 10/1987 | Masquelier |
| 6,638,971 B2 * | 10/2003 | Romanczyk et al. ........ 514/456 |
| 2005/0175565 A1 * | 8/2005 | Duranton et al. ............ 424/70.1 |
| 2008/0044453 A1 * | 2/2008 | Kobayashi ........... A61K 31/353 |
| | | 424/439 |
| 2011/0039923 A1 | 2/2011 | Bhaskaran et al. |

FOREIGN PATENT DOCUMENTS

| JP | 200663053 A | 3/2006 |
| WO | 0063201 A1 | 10/2000 |
| WO | 2006117405 A1 | 11/2006 |
| WO | 2010075611 A1 | 7/2010 |

OTHER PUBLICATIONS

Trüeb. Chemotherapy-Induced Alopecia. Semin Cutan Med Surg (2009), vol. 28, p. 11-14).*
Rohdewald P.: "A Review of the French Maritime Pine Bark Extract (Pycnogenol®), a Herbal Medication with a Diverse Clinical Pharmacology" International Journal of Clinical Pharmacology and Therapeutics, 2002, vol. 40, No. 4, pp. 158-168.
International Search Report for PCT/IB2012/053646 dated Oct. 17, 2012.

* cited by examiner

*Primary Examiner* — Kendra D Carter
*Assistant Examiner* — Taina D Matos Negron
(74) *Attorney, Agent, or Firm* — Hauptman Ham, LLP; Sean A. Passino

(57) ABSTRACT

The present disclosure is related to management of chemotherapy induced side effects namely cachexia and alopecia by administering a pharmaceutical composition comprising pentameric type A procyanidin flavonoid, trimeric procyanidin flavonoid and tetrameric procyanidin flavonoid, optionally along with pharmaceutical excipients.

5 Claims, No Drawings

METHOD OF MANAGING CHEMOTHERAPY INDUCED ALOPECIA OR CACHEXIA OR BOTH

TECHNICAL FIELD

The present disclosure is related to management of chemotherapy induced cachexia and alopecia.

BACKGROUND AND PRIOR ART

The term "Chemotherapy" refers to treatment with a chemical agent. Chemotherapy can be defined as the utilization of pharmaceuticals specifically designed to target, combat and destroy diseased cells, according to the American Cancer Society.

Chemotherapy is one of the methods of treatment for Cancers, Autoimmune diseases such as Systemic sclerosis, Lupus Erythematosus, Rheumatoid Arthritis, Vasculitis and certain viral infections.

In case of cancer, the chemotherapeutic agent destroys cancer cells by targeting rapidly dividing cells in the body. Due to lack of specificity to cancer cells, the toxic effects of chemotherapy are also seen in other rapidly dividing non-cancerous cells. Blood cells, cells in the mouth, intestinal tract, nose, nails and hair are some of the rapidly dividing cells in the body. Destruction of normal cells in the body gives rise to side effects like alopecia, cachexia, anemia, leucopenia, neutropenia etc. These side effects limit the effectiveness of chemotherapy and increase risk of dose reduction, which directly impacts a patient's chances of survival against cancer.

In case of autoimmune diseases, Cyclophosphamide (CPM) has been used in Systemic sclerosis (Patricia Andrade de Macedo, 2009). It is an immunosuppressive alkylating agent which suppresses and modulates lymphocytes by means of the modification of cellular components.

Complete hair loss is an unusual complication of CPM in the doses typically used to treat Vasculitis. More commonly, mild to moderate thinning of the hair occurs.

In viral infections, Interferon alfa-2b acts as biological response modifier used in the treatment of Venereal warts, Hepatitis B, Chronic Hepatitis C and AIDS-related Kaposi's Sarcoma. Interferons (IFNs) are proteins made and released by host cells in response to the presence of pathogens such as viruses, bacteria, parasites or tumor cells.

Interferon alfa-2b also acts as an antineoplastic agent in the treatment of Hairy Cell Leukemia, Melanoma and Mycosis Fungoides. Cachexia and Alopecia are two of the many side effects of this drug.

Cachexia or weight loss is a predominant side effect seen in all patients undergoing chemotherapy treatment. Cachexia is described as a syndrome of progressive weight loss, reduction in food intake, and persistent erosion of host body cell mass in response to a malignant growth. This condition is further worsened by chemotherapy. Chemotherapy treatment comprising anthracyclines, aromatase inhibitors, bleomycins, cytotoxic nucleosides, discodermolides, diynenes, epothilones, mitomycins, podophyllotoxins, pteridines, taxanes, vinca alkaloids etc., induce cachexia and fatigue in patients. Currently, there are no drugs which can prevent or treat chemotherapy induced cachexia. Parenteral nutritional support along with manipulation of host metabolism using insulin therapy or exercise can help in maintaining body weight. However, these methods do not prevent cachexia induced by chemotherapy.

Hair loss or Alopecia is yet another major side effect of chemotherapy. It is considered to be one of the most traumatic factors amongst patients undergoing chemotherapy, since it negatively impacts an individual's perception of appearance, body image and self-esteem. Hair loss or alopecia in patients undergoing chemotherapy is caused by toxic effects of chemotherapy on rapidly dividing cells that arrest mitotic activity in the hair follicles and influence hair shedding. It is mostly a reversible condition and limited to the duration of the chemotherapy treatment cycles.

The extent of hair loss depends on the type of chemotherapy used. Chemotherapy treatment comprising actinomycin-D, cyclophosphamide, bleomycin, daunorubicin, doxorubicin, epirubicin, irinotecan, paclitaxel, docetaxel, topotecan, vindesine etc., causes complete alopecia. Relatively less severe hair loss is seen with chemotherapy drugs like amsacrine, bleomycin, busulphan, capecitabine eribulin, etoposide, fludarabine, fluorouracil, gemcitabine, ifosfamide, lomustine, melphalan, mitoxantrone, thiotepa, vincristine, vinblastine, vinca alkaloids, vinorelbine etc. Drugs like cisplatin, carboplatin, carmustine, cytarabine, mercaptopurine, methotrexate, mitomycin, procarbazine, raltitrexate, sreptozotocin etc., rarely cause hair loss. However many of them cause thinning of hair along with change in color and texture of hair. Chemotherapy treatment comprises a cocktail of these drugs and nearly 65% of patients undergoing chemotherapy treatment experience alopecia.

At present, no approved pharmacological intervention exists to circumvent chemotherapy induced hair loss. Scalp cooling is practised as a major approach to minimize hair loss in patients undergoing chemotherapy. But the hypothermia causes uncomfortable chillness and headaches in patients. Topical application of drugs like Minoxidil and Finasteride can reduce the severity or shorten the duration of hair loss.

However, these drugs are developed for androgenic alopecia and their efficacy varies drastically in chemotherapy induced alopecia.

With the increasing number of patients undergoing chemotherapy, there is a need for interventions which can prevent or minimize these unaddressed side effects of chemotherapy. Most of the patients undergoing chemotherapy experience these side effects. The occurrence of these side effects of Chemotherapy depends upon the dose, route of administration and cytotoxicity of individual drug, combination of drugs, and other individual characteristics. For example, the anti-cancer drug Cyclophosphamide is widely used along with any other drug in combination in Lymphomas, Lung Cancer, Hodgkin's lymphoma, Non-Hodgkin's lymphoma as well as for autoimmune diseases such as Vasculitis. The drugs used in for chemotherapy treatment are generally cytotoxic in nature and therefore eliminate fast cells such as hair follicles.

Androgenic Alopecia (normal hair loss) and Anagen Effluvium (Chemo induced hair loss) are placed under different categories according to the ICD (International Classification of Diseases). Drugs like Minodixil work on normal hair loss but fail in the treatment of chemo induced hair loss. The instant invention is not related to hair growth. It works for the treatment of hair loss caused due to chemotherapy.

Hence, the present invention addresses these issues and provides a method of management of chemotherapy induced side effects namely cachexia and alopecia using a composition comprising pentameric type A procyanidin, trimeric procyanidin and tetrameric procyanidin, optionally along with pharmaceutical excipient to a subject in need thereof Bhaskaran et al. (U.S. 2011/0039923 A1) discloses a composition comprising pentameric procyanidin flavonoid of concentration ranging from about 55% w/w to about 99% w/w, trimers and tetramers each at a concentration ranging from about 0.5% w/w to about 35% w/w. This document also discloses a process for preparation of the said composition from plant sources namely Cinnamon, Litchi and Arachis. Further, this document teaches use of the said composition for treatment and management of infections like HIV, AIDS and Influenza virus. However, this document does not suggest or teach the use of the said composition in prevention and management of chemotherapy induced cachexia and alopecia.

STATEMENT OF DISCLOSURE

Accordingly, the present disclosure relates to a method of managing chemotherapy induced alopecia or cachexia or both, using composition comprising pentameric type A procyanidin, trimeric procyanidin and tetrameric procyanidin, optionally along with pharmaceutical excipient.

DETAILED DESCRIPTION

The present disclosure relates to a method of managing chemotherapy induced alopecia or cachexia or both, using a composition comprising pentameric type A procyanidin, trimeric procyanidin and tetrameric procyanidin, optionally along with pharmaceutical excipient.

In an embodiment of the present disclosure, the pentameric type A procyanidin is at concentration ranging from about 55% w/w to about 99% w/w, the trimeric procyanidin and the tetrameric procyanidin are each at concentration ranging from about 0.5% w/w to about 35% w/w; and the pharmaceutical excipient is at concentration ranging from about 0.5% w/w to about 10% w/w.

In another embodiment of the present disclosure, the excipient is selected from group comprising granulating agents, binding agents, lubricating agents, disintegrating agents, sweetening agents, glidants, anti-adherents, anti-static agents, surfactants, anti-oxidants, gums, coating agents, coloring agents, flavouring agents, plasticizers, preservatives, suspending agents, emulsifying agents, plant cellulosic material and spheronization agents or any combination thereof.

In yet another embodiment of the present disclosure, the composition is formulated into dosage forms selected from group comprising tablet, troches, lozenges, aqueous or oily suspensions, capsule, emulsion, spray, drops, dispersible powders or granules, emulsion in hard or soft gel capsules, syrups, elixirs, phytoceuticals, nutraceuticals and food stuffs or any combination thereof.

In still another embodiment of the present disclosure, the composition is administered to subject in need thereof at dose ranging from about 1 mg/kg to about 50 mg/kg, preferably ranging from about 10 mg/kg to about 25 mg/kg of body weight of said subject per day.

In still another embodiment of the present disclosure, the subject is a mammal.

In an embodiment of the present disclosure, the term "managing" or "management" includes preventing and treating of a disease condition or disorder or ill effects or side effects. The term also encompasses maintenance of the optimum state and prevention of further progress in the disease condition or disorder or ill effects or side effects.

In another embodiment of present disclosure, the term "instant composition" refers to pentameric type A procyanidin at concentration ranging from about 55% w/w to about 99% w/w, trimeric procyanidin and tetrameric procyanidin each at concentration ranging from about 0.5% w/w to about 35% w/w; and pharmaceutical excipient at concentration ranging from about 0.5% w/w to about 10% w/w.

In another embodiment of the present disclosure, the instant composition is formulated into a suitable dosage formulation for management of alopecia and cachexia in patients undergoing chemotherapy using a dose ranging from about 1 mg/kg to about 50 mg/kg of body weight of subject per day, preferably ranging from about 10 mg/kg to about 25 mg/kg of body weight of subject per day, or a dosage of about 400 mg thrice a day or any suitable dosage range that a person skilled in the art will know to arrive at.

The invention is further elaborated with the help of following examples. However, these examples should not be construed to limit the scope of the invention.

EXAMPLES

Example 1

Formulation of Instant Composition

The instant composition comprising type A pentameric procyanidin flavonoid of concentration ranging from about 55% w/w to about 99% w/w, trimers and tetramers of procyanidin flavonoid each at concentration ranging from about 0.5% w/w to about 35% w/w is formulated into capsules by blending with 2% w/w of micro crystalline cellulose, 0.5% w/w of crospovidone and 0.2% w/w of magnesium stearate. This mixture is filled in capsules.

Similar formulation of the instant composition is prepared by addition of appropriate excipient(s) selected from group comprising the following: granulating agents, binding agents, lubricating agents, disintegrating agents, sweetening agents, glidants, anti-adherents, anti-static agents, surfactants, anti-oxidants, gums, coating agents, coloring agents, flavouring agents, plasticizers, preservatives, suspending agents, emulsifying agents, plant cellulosic material and spheronization agents or any combination thereof.

In another embodiment of present disclosure, oral formulations of the composition, like tablets, liquid orals, powders or granules are prepared by using above formula and other excipients selected from the group mentioned above.

The formulations prepared by using the instant composition and excipients from the group with a dose ranging from about 1 mg/kg to about 50 mg/kg of body weight of subject, preferably about 10 mg/kg to about 25 mg/kg of body weight show similar efficacy in treatment of the side effects.

In an embodiment of the instant disclosure, Saccharides and their derivatives, Cellulose or Stearic acid are used as pharmaceutically acceptable excipient.

The type of formulation is selected from group consisting of tablet, troches, lozenges, aqueous or oily suspensions, capsule, emulsion, spray, drops, dispersible powders or granules, emulsion in hard or soft gel capsules, syrups, elixirs, phytoceuticals, nutraceuticals and food stuffs or any combination thereof. Depending on the route of administration, different excipients/carriers are used.

In an embodiment of the present disclosure, the instant composition is formulated into syrups or elixirs, the composition ranging from about 1 mg/kg to about 50 mg/kg of body weight of subject, preferably about 10 mg/kg to about 25 mg/kg of body weight.

Those skilled in art will know to choose a suitable formulation of the instant composition for management of alopecia and cachexia in patients undergoing chemotherapy using a dose range from about 1 mg/kg to about 50 mg/kg of body weight of subject, a dose range from about 10 mg/kg to about 25 mg/kg of body weight or a dosage of about 400 mg thrice a day as elucidated in the following examples.

efficacy of the instant composition in reducing cachexia induced by chemotherapy is evaluated. The placebo composition is Dicalcium Phosphate.

Cachexia is monitored in the patients as change in body weight from baseline. Here baseline is defined as the initial body weight at the start of the study. At the start of the study (at baseline) there is no significant difference in the mean body weight in treatment group (58.29 kg) and placebo group (64.19 kg). At the end of the study, this change is significant between the treatment and placebo group. Patients in the treatment group showed overall maintenance of body weight. Increasing trends in terms of gain in body weight in the treatment group at the end of each chemotherapy session demonstrate significant prevention of weight loss as compared to the placebo. Cachexia in terms of weight loss is significantly prevented or reduced by the instant composition.

TABLE 1

EFFECT ON CHEMOTHERAPY INDUCED CACHEXIA
Mean change in body weight from Baseline (kg) ± SD

| Instant Composition (n = 17) | | | | Placebo (n = 17) | | | |
| --- | --- | --- | --- | --- | --- | --- | --- |
| Visit 1 | Visit 2 | Visit 3 | Visit 4 (end of study) | Visit 1 | Visit 2 | Visit 3 | Visit 4 (end of study) |
| ↑0.04 ± 0.09 | ↑0.38 ± 1.15* | ↑0.28 ± 1.28* | ↑0.63 ± 1.03* | ↓0.15 ± 0.57 | ↓0.43 ± 0.84 | ↓0.53 ± 1.0 | ↓0.49 ± 0.97 |

Data is represented as Mean ± SD;
SD = Standard Deviation,
↑ shows increase in body weight,
↓ shows decrease in body weight.
Data was analyzed using t-test;
*$P < 0.05$ as compared to Placebo group, at respective visits.

In an embodiment of the present disclosure, the term "managing" or "management" includes preventing and treating of a disease condition or disorder or ill effects or side effects. The term also encompasses maintenance of the optimum state and prevention of the further progress in the disease condition or disorder or ill effects or side effects.

Example 2

Effect on Chemotherapy induced Side Effects-Cachexia in Cancer Patients

In order to elucidate the effect of instant composition on chemotherapy induced cachexia in cancer patients, a double-blind, randomized, placebo-controlled study is conducted in 34 female patients with breast cancer undergoing chemotherapy.

Patients with histologically or cytologically confirmed primary carcinoma of the breast are chosen for the study. The presence of the carcinoma is confirmed by Core biopsy, Needle Biopsy or Fine—needle Aspiration Cytology. The selected patients with breast cancer are being treated by either CAF (Cyclophosphamide, Adriamycin, 5-Flurouracil) or AT (Adriamycin, Taxotere (Docetaxel)) regimen. Thus, selected patients show the side effects like Alopecia and Cachexia and are being treated by different regimens. These drugs are not restricted to use in cancer and are also being used in different chemotherapy regimens like Autoimmune diseases, Viral infections etc.

Capsules of instant composition formulated in example 1 are administered at dose of about 400 mg thrice daily for 3 months during 4 successive chemotherapy sessions. The As shown in Table 1, at visit 4, the treatment group showed significant increase (P<0.05) in body weight as compared to placebo group. The example shows that Cachexia (weight loss) is significantly prevented or reduced by the instant composition.

Example 3

Effect on Chemotherapy Induced Side Effects—Alopecia; With Respect to Hair Density Efficacy of the instant composition in chemotherapy induced alopecia is evaluated. The instant composition is administered at dose of about 10 to about 25 mg/kg of body weight daily to 17 cancer patients undergoing chemotherapy for 3 months during 4 successive chemotherapy sessions. 17 patients are in the placebo—controlled group. The placebo composition is Dicalcium Phosphate.

Chemotherapy induced alopecia is monitored using parameters like hair density and percent and hair in anagen and telogen phases. Trichoscan (instrument for qualitative analysis of hair) is used to measure hair parameters of patients in treatment and placebo group. Hair density is defined as the number of hair per sq. cm, and it has an inverse correlation with alopecia. A reduction in hair density (hair thinning) shows increased alopecia.

As shown in Table 2, at visit 4, no significant change is observed in the mean hair density among patients in the treatment group from baseline. However significant reduction in mean hair density is observed in the placebo group from baseline. This shows that chemotherapy induced alopecia is significantly reduced by the instant composition.

TABLE 2

EFFECT ON CHEMOTHERAPY INDUCED ALOPECIA (HAIR DENSITY)

| | Instant Composition (n = 17) | | Placebo (n = 17) | |
|---|---|---|---|---|
| Parameters | Baseline | Visit 4 (end of study) | Baseline | Visit 4 (end of study) |
| Hair Density (hair/cm$^2$) | 44.53 ± 16.09 | 21.5 ± 23.15$^{ns}$ | 37.12 ± 12.93 | ↓11.3 ± 12.63* |

Data is represented as Mean ± SD;
Data was analyzed using Mann Whitney U test.
*$P < 0.05$ as compared to baseline value of respective groups.
↓shows decrease in hair density,
$^{ns}$not significant Example 4

Effect on Chemotherapy Induced Side Effects—Alopecia; With Respect to Anagen and Telogen Phase In continuation to Example 3, the count of hair in anagen phase reflects the hair that is in the phase of active growth and loss of hair in anagen phase indicates alopecia. Telogen is the resting phase of the hair, after which the hair is shed. Loss of hair in telogen phase also contributes to alopecia.

TABLE 3

EFFECT ON ANAGEN AND TELOGEN HAIR %

| | Treatment (n = 17) | | Placebo (n = 17) | |
|---|---|---|---|---|
| Parameters | Baseline | Visit 4 | Baseline | Visit 4 |
| % Anagen Hair | 74.29 ± 33.45 | 50.0 ± 45.61$^{ns}$ | 90.63 ± 15.69 | ↓39.09 ± 42.06$^{\#}$ |
| % Telogen Hair | 21.43 ± 28.78 | 49.09 ± 45.49$^{ns}$ | 10.0 ± 16.33 | ↑57.27 ± 41.01$^{\#}$ |

Data is represented as Mean ± SD;
Data was analyzed using Mann Whitney U test;
$^{\#}P < 0.05$ as compared to baseline value of respective groups.
↑shows Increase in % hair
↓shows Decrease in % hair
$^{ns}$not significant As shown in Table 3, at visit 4, the patients in the treatment group showed 24% decrease in percent anagen hair which is not significant when compared with the baseline. On the other hand, at visit 4, patients in placebo group showed significant (P<0.05) decrease in percent anagen hair (decrease by 51%) as compared with baseline. This shows that the instant composition sustains active hair growth phase (anagen) thus preventing further stages of alopecia.

As shown in Table 3, at visit 4, the patients in the treatment group showed increase (by 27%) in percentage of telogen hair which is not significant when compared with the baseline. On the other hand, at visit 4, patients in placebo group showed significant (P<0.05) increase in percent telogen hair (increase by 47%) when compared with baseline. This shows that the instant composition prevents hair loss in telogen phase and thus prevents alopecia.

Hence, the instant composition is effective in management of chemotherapy induced cachexia and alopecia in patients undergoing chemotherapy treatments.

In an embodiment of the present disclosure, the term "managing" or "management" includes preventing and treating of a disease condition or disorder or ill effects or side effects. The term also encompasses maintenance of the optimum state and prevention of the further progress in the disease condition or disorder or ill effects or side effects.

The unique and advantageous features of the instant invention are:

The instant composition works on two chemotherapy side effects, Alopecia and Cachexia at the same time while there is no prior art showing one common drug effective for these two different side effects.

The instant composition does not show any side effects (e.g. Finasteride, a drug used for treatment of Male Pattern Baldness, is known to increase the risk of prostate cancer).

We claim:

1. A method of managing chemotherapy induced alopecia or cachexia or both, wherein said method consists of administering a composition consisting of pentameric type A procyanidin, trimeric procyanidin and tetrameric procyanidin, optionally using a pharmaceutical excipient, to a subject in need thereof;
wherein the pentameric type A procyanidin is at concentration ranging from about 55% w/w to about 99% w/w, the trimeric procyanidin and the tetrameric procyanidin are each at concentration ranging from about 0.5% w/w to about 35% w/w, and the pharmaceutical excipient is at concentration ranging from about 0.5% w/w to about 10% w/w.

2. The method as claimed in claim 1, wherein the excipient is selected from the group comprising granulating agents, binding agents, lubricating agents, disintegrating agents, sweetening agents, glidants, anti-adherents, anti-static agents, surfactants, anti-oxidants, gums, coating agents, coloring agents, flavouring agents, plasticizers, preservatives, suspending agents, emulsifying agents, plant cellulosic material and spheronization agents or any combination thereof.

3. The method as claimed in claim 1, wherein the composition is formulated into a dosage form selected from the group comprising of a tablet, troches, lozenges, aqueous or oily suspensions, capsule, emulsion, spray, drops, dispersible powders or granules, emulsion in hard or soft gel capsules, syrups, elixirs, phytoceuticals, nutraceuticals and food stuffs or any combination thereof.

4. The method as claimed in claim 1, wherein the composition is administered to subject in need thereof, at dose ranging from about 1 mg/kg to about 50 mg/kg, preferably ranging from about 10 mg/kg to about 25 mg/kg of body weight of said subject per day.

5. The method as claimed in claim 4, wherein the subject is a mammal.

* * * * *